(12) United States Patent
Sealfon

(10) Patent No.: US 6,926,706 B1
(45) Date of Patent: Aug. 9, 2005

(54) MECHANICAL VARIABLE RATE FLOW CONTROL FOR A CONSTANT PRESSURE IV DELIVERY SYSTEM

(75) Inventor: Andrew Sealfon, Chester, NY (US)

(73) Assignee: Repro-Med Systems, Inc., Chester, NY (US)

( * ) Notice: Subject to any disclaimer, the term of this patent is extended or adjusted under 35 U.S.C. 154(b) by 0 days.

(21) Appl. No.: 10/621,753

(22) Filed: Jul. 18, 2003

Related U.S. Application Data

(60) Provisional application No. 60/396,610, filed on Jul. 19, 2002.

(51) Int. Cl.[7] .............................................. A61M 31/00
(52) U.S. Cl. ..................................................... 604/500
(58) Field of Search ........................... 604/500, 30, 32, 604/33, 248, 245, 246, 247, 131, 151

(56) References Cited

U.S. PATENT DOCUMENTS 5,318,515 A   6/1994   Wilk

*Primary Examiner*—Kevin C. Sirmons
(74) *Attorney, Agent, or Firm*—Myron Amer, P.C.

(57) ABSTRACT

In an IV delivery system, a flow control knob which is rotated to establish camming contact with pistons that operate valves, as a substitute improvement for finger manipulation of the valves, which is prone to switch selection error.

Figures 1, 2:
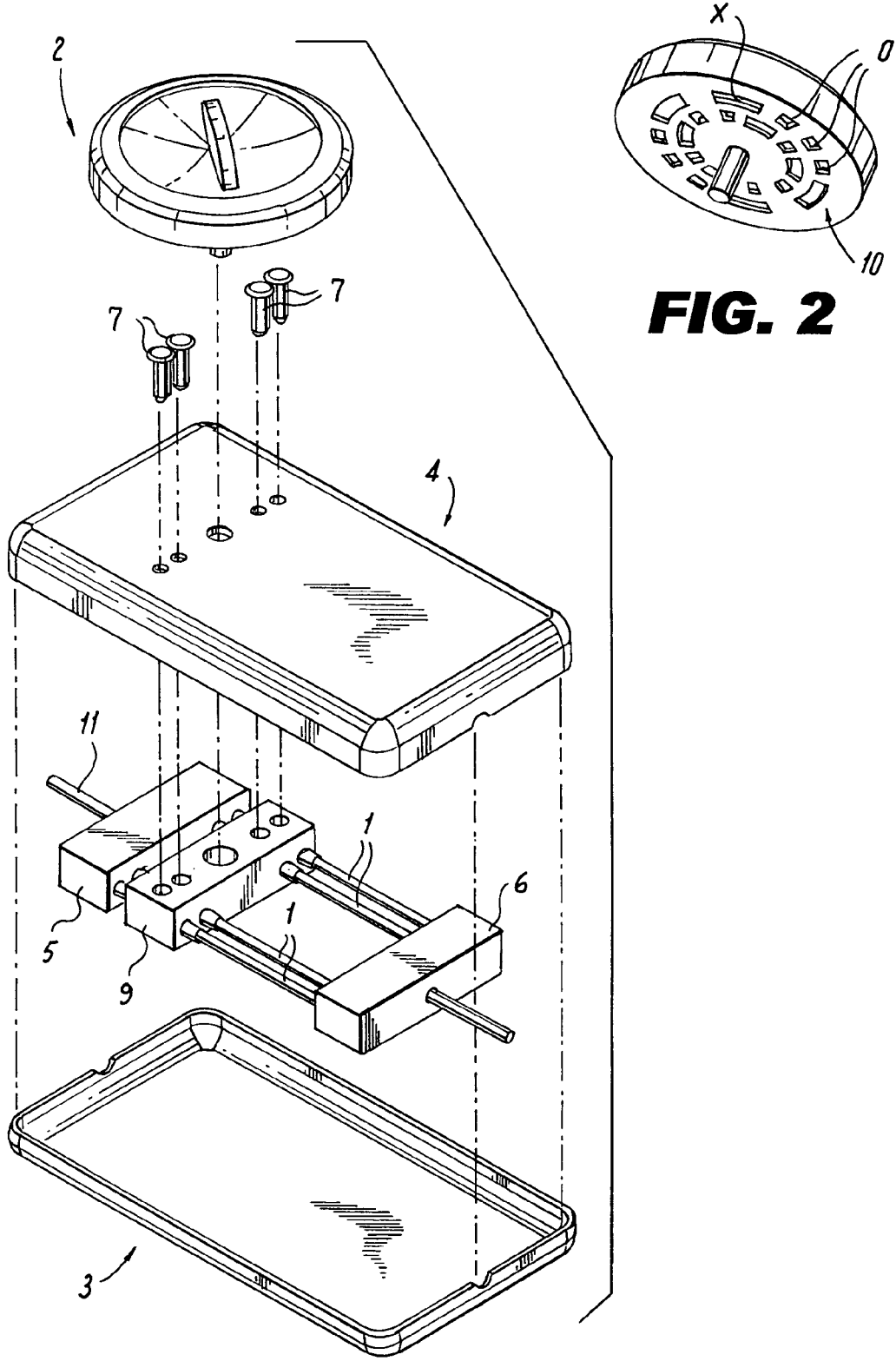

1 Claim, 1 Drawing Sheet

MECHANICAL VARIABLE RATE FLOW CONTROL FOR A CONSTANT PRESSURE IV DELIVERY SYSTEM

CROSS REFERENCE TO RELATED APPLICATIONS

This application claims the benefit of U.S. Provisional Patent Application No. 60/396,610, filed on Jul. 19, 2002, the contents of which are incorporated herein by reference thereto.

The present invention relates generally to improvements concerned with two popular methods to control flow with a fixed rate of flow. One is with capillary tubes and the other uses restrictive flow tubing sets. The improvements address the problem of how to provide a wide range of fixed flows accurately using the available technology.

EXAMPLE OF THE PRIOR ART

U.S. Pat. No. 5,318,515 for "Intravenous Flow Regulator Device And Associated Method" issued to Wilk discloses the use of fixed, different flow passages with flow rates such as 25 cc/hr, 50 cc/hr, 100 cc/hr and 200 cc/hr that are opened and closed by manually operated switches to achieve a range of flow rates. A drawback in Wilk however is that an operating mode of opening and closing switches is undesirable not only because it is implemented manually, but also because it cannot be readily correlated to ascending and descending flow rates except by reference to written instructions, and the correlation noted is undesirable in making flow rate adjustments.

Broadly, it is an object of the present invention to overcome the foregoing and other shortcomings of the prior art.

More particularly, it is an object to obtain the switch operation which provides the flow control in a rotational rather than a finger manipulation, and to thereby obviate human error, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

FIG. 1 is an exploded perspective view of the unassembled components of a variable rate flow control for a constant pressure IV delivery system according to the present invention; and FIG. 2 is an isolated view of a knob component of FIG. 1, illustrating further structural details.

The illustrated, preferred embodiment demonstrates how four capillaries (1) functioning as flow restrictions are connected in a binary fashion to permit 15 different flow rates in one assembly, as illustrated in FIG. 1. It is to be understood that each capillary (1) has a binary numerical value, i.e., 1, 2, 4, 8 and can be allowed to flow by pressing on the pistons (7) which open normally-closed spring operated valves (not shown) housed in the valve block (9). The inlet 11 from an IV bag (not shown) is on the left in fluid communication with the common manifold inlet (5) for the four capillaries (1).

The knob (2) selects any flow, in this example, from 1 ml/hr to 15 ml/hr or off, i.e., no valves open for flow, or a total of 15 positions. That is, if the four tubes (1) in this example are made to flow with the first (encountered proceeding from the left) tube at 1 ml/hr, the second at 2 ml/hr, the third at 4 ml/hr and the fourth at 8 ml/hr, one can set flow rates from 1 ml/hr, the first capillary tube by itself to, for example 10 ml/hr, combining 2 ml/hr with 8 ml/hr, all the way up to 15 ml/hr, i.e., 1+2+4+8=15. With X signifying an open valve and 0 closed, the 15 positions are: 1=X000; 2=0X00; 3=XX00; 4=00X0; 5=X0X0; 6=0XX0; 7=XXX0; 8=000X; 9=X00X; 10=0X0X; 11=XX0X; 12=00XX; 13=X0XX; 14=0XXX; 15=XXXX.

By turning the knob (2) each flow setting can be accurately selected and using the bosses (10), correlated by position to open the normally closed valves or not by camming contact against the pistons (7) or avoiding such contact, the former bosses (10) identified as exemplary by the reference letter X and the latter bosses (10) by the reference letter 0, are provided on the underside of the knob (2), the exemplary binary position illustrated in FIG. 2 being position 1 or X000. In this manner the rotational operating mode of knob (2) depresses the appropriate piston(s) (7) to generate the selected flow automatically, thereby obviating manual operation of on-off switches as in the noted Wilks patent.

In a preferred embodiment the knob (2) will have a pointer that will align with specific flow rates from 0–15 ml/hr in 1 ml/hr increments. Also, the components of FIG. 1 in assembled relation will be housed in a thin clamshell of cover (4) and base (3) maintaining a convenient flat profile, making it easy to inconspicuously attach to a patient's arm. A locking mechanism optionally can be added to the device (4), (3) to prevent patient tampering when used in ambulatory treatments.

In use, the system can generate additional flow rates by adding additional capillaries (1) with selected fluid restrictions. For example, 5 capillaries would generate a total of 32 different flow rates, calculated at 2 to the fifth power. Or if each capillary was incremented by 5 ml/hr (5, 10, 15, 20) the user could have variable flows from 5 ml/hr to 75 ml/hr in 5 ml/hr increments.

While the variable rate flow control for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. An improvement in a method of providing a desired combined flow rate through four capillaries of medicant from an IV source to a catheter connected to a patient in a step of which finger manipulated valves are selectively opened and not-opened to achieve said flow rate, wherein the improvement comprises the steps of:

A. arranging said four capillaries in flow paths extending between said IV source to a patient for flowing medicant therealong to normally-closed outlet valves;

B. arranging pistons in said flow paths to partake of descending movement effective to open said normally-closed outlet valves;

C. employing a rotational operational mode in a piston-contacting knob having a rotational degree of movement effective to urge in valve-opening descending movement pistons effective to provide a desired flow rate; and D. selecting by positioning on an underside of said piston-contacting knob locations of bosses effective to establish a camming engagement with those of said pistons to produce flow through said capillaries at said desired flow rate;

whereby there is substituted rotational knob movement for individual finger manipulation of switches as might be prone to a switch selection error.

\* \* \* \* \*